US00PP14315P29

(12) United States Plant Patent
Dümmen

(10) Patent No.: US PP14,315 P2
(45) Date of Patent: Nov. 25, 2003

(54) POINSETTIA PLANT NAMED 'DUEPREMWI'

(50) Latin Name: *Euphorbia pulcherrima Willd.*
Varietal Denomination: Duepremwi

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/228,481

(22) Filed: Aug. 27, 2002

(51) Int. Cl.[7] ..... A01H 5/00
(52) U.S. Cl. ..... Plt./304
(58) Field of Search ..... Plt./304

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Poinsettia plant named 'Duepremwi', characterized by its inflorescences with pale yellow-colored flower bracts; dark green-colored leaves; uniform and rounded plant habit; freely branching habit; early flowering habit; and excellent post-production longevity.

1 Drawing Sheet

Botanical classification/cultivar denomination: *Euphorbia pulcherrima Willd.* cultivar Duepremwi.

BACKGROUND OF THE INVENTION

The present Invention relates to a new and distinct cultivar of Poinsettia plant, botanically known as *Euphorbia pulcherrima Willd.,* and hereinafter referred to by the name 'Duepremwi'.

The new Poinsettia is a product of a mutation induction program conducted by the Inventor in Rheinberg, Germany. The objective of the program is to create new Poinsettia cultivars with uniform plant habit and attractive flower bract coloration.

The new Poinsettia originated by exposing unrooted cuttings of a proprietary *Euphorbia pulcherrima Willd.* selection identified as code number E-16-18, not patented, to gamma radiation in Rheinberg, Germany. The new Poinsettia was discovered and selected by the Inventor as a single plant within a population of irradiated plants in a controlled environment in Rheinberg, Germany in December, 2000. The selection of this plant was based on its attractive flower bract coloration.

Asexual reproduction of the new Poinsettia by vegetative terminal cuttings taken at Rheinberg, Germany since March, 2001, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duepremwi'. These characteristics in combination distinguish 'Duepremwi' as a new and distinct cultivar:

1. Inflorescences with pale yellow-colored flower bracts.
2. Dark green-colored leaves.
3. Uniform and rounded plant habit.
4. Freely branching habit.
5. Early flowering habit; response time, about eight weeks.
6. Excellent post-production longevity.

Plants of the new Poinsettia differ primarily from plants of the parent, the selection E-16-18, in flower bract color. Plants of the new Poinsettia differ primarily from plants of the Poinsettia cultivar Dueprempink, disclosed in a U.S. Plant Patent application filed concurrently, in flower bract color.

Plants of the new Poinsettia can be compared to plants of the cultivar Fiscor Creme, disclosed in U.S. Plant Pat. No. 10,824. In side-by-side comparisons conducted in Rheinberg, Germany, plants of the new Poinsettia differed from plants of the cultivar Fiscor Creme in the following characteristics:

1. Plants of the new Poinsettia were not as broad as plants of the cultivar Fiscor Creme.
2. Plants of the new Poinsettia were more densely foliated than plants of the cultivar Fiscor Creme.
3. Plants of the new Poinsettia had larger leaves than plants of the cultivar Fiscor Creme.
4. Plants of the new Poinsettia flowered earlier than plants of the cultivar Fiscor Creme.
5. Plants of the new Poinsettia had larger inflorescences with more flower bracts per inflorescence than plants of the cultivar Fiscor Creme.
6. Flower bracts of plants of the new Poinsettia were lighter in color than flower bracts of plants of the cultivar Fiscor Creme.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph differ slightly from the color values cited in the detailed botanical description which accurately describe the colors of the new Poinsettia. The photograph comprises a side perspective view of a single flowering plant of 'Duepremwi' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photograph, following observations and averaged measurements describe plants grown in Rheinberg, Germany during the winter under commercial practice in a glass-covered greenhouse with day and night temperatures about 22° C. and light levels about 4,500 lux. Single plants were grown in 13-cm containers and pinched once about five weeks after planting. Plants were flowered under natural season short day/long night conditions. Plants were about 16 weeks from unrooted cuttings when the photograph and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima Willd.* cultivar Duepremwi.

Parentage: Induced mutation of a proprietary selection of *Euphorbia pulcherrima Willd.* identified as code number E-16-18, not patented.

Propagation:

*Type cutting.*—Vegetative terminal cuttings.

*Time to initiate roots.*—Summer: About 9 days at 22° C. Winter: About 13 days at 22° C.

*Time to develop roots.*—Summer: About 21 days at 22° C. Winter: About 28 days at 22° C.

*Root description.*—Thick, fibrous and white in color.

*Rooting habit.*—Freely branching.

Plant description:

*Plant form.*—Inverted triangle, top of plant rounded.

*Growth habit.*—Upright and uniform plant habit.

*Plant height.*—About 21 cm.

*Plant diameter or spread.*—About 37 cm.

*Lateral branch description.*—Quantity per plant: Freely branching habit; about six lateral branches develop after pinching. Length: About 18 cm. Diameter: About 6 mm. Internode length: About 1.5 cm. Color: 137A.

*Foliage description.*—Arrangement: Alternate, single. Quantity of leaves per lateral branch: About 12. Length: About 12.9 cm. Width: About 9.3 cm. Shape: Mostly ovate. Apex: Apiculate. Base: Obtuse. Margin: Entire with irregular lobing. Venation pattern: Pinnate. Texture, upper and lower surfaces: Glabrous, smooth. Surface: Mostly flat. Color: Young foliage, upper surface: 141B. Young foliage, lower surface: 138A. Fully expanded foliage, upper surface: 139A. Fully expanded foliage, lower surface: 138A. Venation, upper surface: 146C. Venation, lower surface: 144B. Petiole: Length: About 4.3 cm. Diameter: About 3 mm. Texture, upper and lower surfaces: Glabrous, smooth. Color, upper and lower surfaces: 144B.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about eight weeks. Post-production longevity: Plants of the new Poinsettia maintain good substance and bract color for about eight weeks under interior conditions and about twelve weeks under greenhouse conditions.

*Quantity of inflorescences per plant.*—One per lateral branch, about six.

*Inflorescence size.*—Diameter: About 24 cm. Height (depth): About 3.5 cm.

*Flower bracts.*—Quantity of flower bracts per inflorescence: About 20. Length, largest bracts: About 11.8 cm. Width, largest bracts: About 7.7 cm. Shape: Mostly ovate. Apex: Apiculate. Base: Obtuse. Margin: Entire with irregular lobing. Texture, upper and lower surfaces: Glabrous, velvety. Surface: Rugose. Orientation: Mostly horizontal. Color: Developing bracts, upper and lower surfaces: 2D. Fully developed bracts, upper and lower surfaces: 2D; color does not fade with subsequent development. Venation, upper and lower surfaces: Same as lamina. Bract petiole: Length: About 2.7 cm. Diameter: About 2 mm. Texture, upper and lower surfaces: Glabrous, smooth. Color, upper and lower surfaces: 144B.

*Cyathia.*—Quantity of cyathia per corymb: About 12. Diameter of cyathia cluster: About 3 cm. Length: About 8 mm. Diameter: About 6 mm. Shape: Ovoid. Color, immature: 144B. Color, mature: 144D. Peduncle: Length: About 3 mm. Diameter: About 2.5 mm. Strength/aspect: Strong, curved. Color: 144B. Stamens: Quantity of stamens and staminodes per cyathium: About 40. Anther shape: Oval. Anther length: About 0.7 mm. Anther color: 9A. Amount of pollen: Abundant. Pollen color: 14A. Pistils: Quantity of pistils per cyathium: One. Pistil length: About 1.1 cm. Style length: About 5 mm. Style color: 144C. Stigma color: 144C. Ovary color: 144B. Nectaries: Quantity of nectaries per cyathium: One. Length: About 6 mm. Color: 15A.

Disease/pest resistance: Resistance to pathogens and pests common to Poinsettias has not been observed on plants grown under commercial conditions.

Temperature tolerance: Plants of the new Poinsettia have been observed to tolerate temperatures from 12 to 40° C.

It is claimed:

1. A new and distinct cultivar of Poinsettia plant named 'Duepremwi', as illustrated and described.

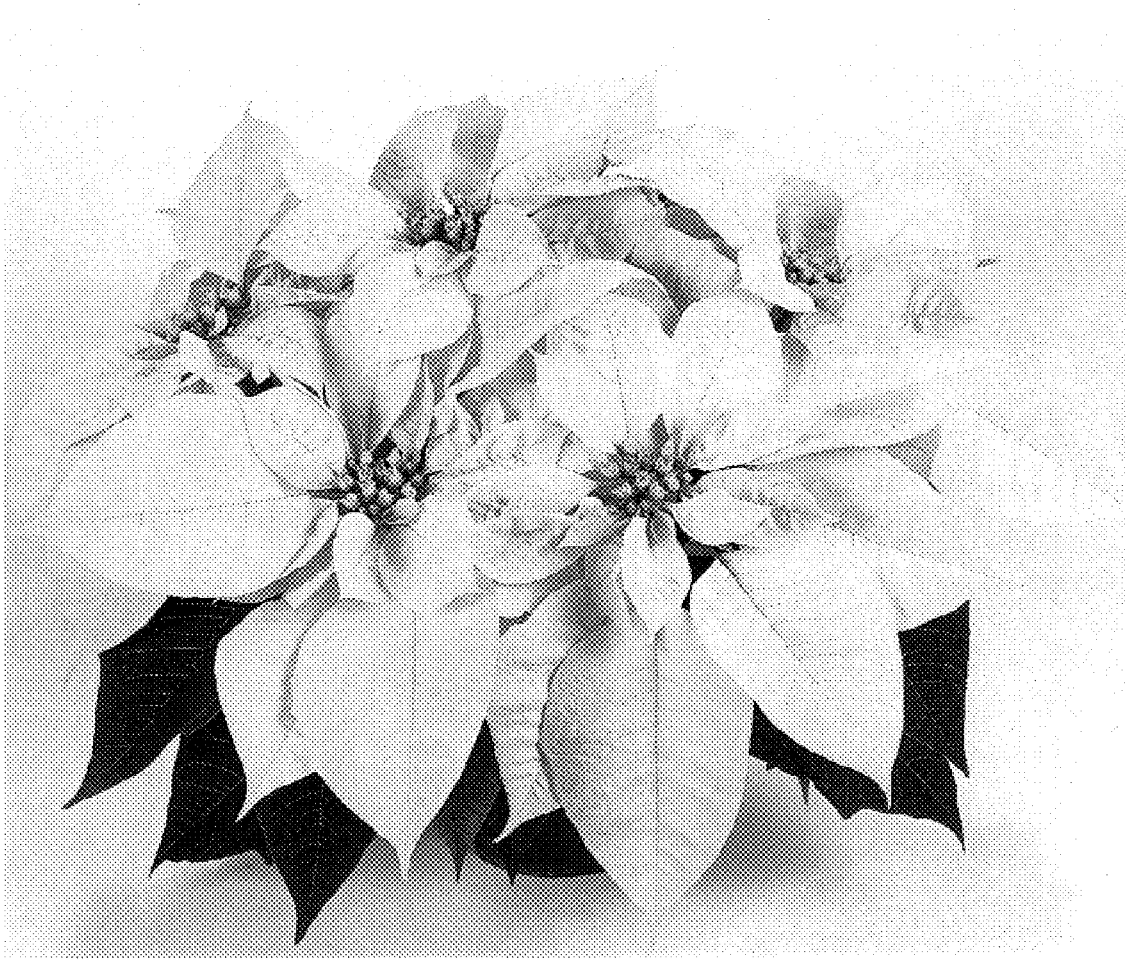

* * * * *